(12) United States Patent
Fritz et al.

(10) Patent No.: US 10,501,394 B2
(45) Date of Patent: Dec. 10, 2019

(54) METHOD AND SYSTEM FOR OBTAINING DIMETHYL ETHER FROM SYNGAS

(71) Applicant: LINDE AKTIENGESELLSCHAFT, Munich (DE)

(72) Inventors: Helmut Fritz, Munich (DE); Thomas Bartesch, Glonn (DE); Clara Delhomme, Munich (DE); Andreas Peschel, Wolfratshausen (DE); Johannes Fendt, Munich (DE); Harald Klein, Wolfratshausen (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 447 days.

(21) Appl. No.: 15/111,601

(22) PCT Filed: Jan. 5, 2015

(86) PCT No.: PCT/EP2015/000007
§ 371 (c)(1),
(2) Date: Jul. 14, 2016

(87) PCT Pub. No.: WO2015/113727
PCT Pub. Date: Aug. 6, 2015

(65) Prior Publication Data
US 2016/0326078 A1    Nov. 10, 2016

(30) Foreign Application Priority Data

Jan. 28, 2014    (EP) ..................................... 14000295

(51) Int. Cl.
*C07C 41/01*    (2006.01)
*C07C 41/09*    (2006.01)
(Continued)

(52) U.S. Cl.
CPC .............. *C07C 41/01* (2013.01); *C07C 27/06* (2013.01); *C07C 41/09* (2013.01)

(58) Field of Classification Search
CPC .................................. C07C 41/01; C07C 27/06
See application file for complete search history.

(56) References Cited

U.S. PATENT DOCUMENTS 6,191,175 B1    2/2001  Haugaard et al.
2007/0078285 A1*  4/2007  Dagle ..................... C07C 41/01
                                              568/698
2013/0030063 A1    1/2013  Randhava et al.

FOREIGN PATENT DOCUMENTS

CN    1413974 A     4/2003
EP    1026141 A1    8/2000
JP    2001070793 A  3/2001

OTHER PUBLICATIONS

DME—the new wonder fuel?, Nitogen & Methanol No. 260, Nov.-Dec. 2002, pp. 25-31.
(Continued)

*Primary Examiner* — Medhanit W Bahta
(74) *Attorney, Agent, or Firm* — Millen White Zelano & Branigan, PC

(57) ABSTRACT

A process is proposed for production of dimethyl ether (DME) from synthesis gas (SG), in which at least one feed stream formed from synthesis gas (SG) is subjected to at least one synthesis step, in which components present in the feed stream are at least in part converted to dimethyl ether (DME), wherein at least one crude product stream is obtained which contains at least dimethyl ether (DME) and the unreacted components of the feed stream. The feed stream contains at least hydrogen, carbon monoxide and carbon dioxide, and has a stoichiometric number of 2.0 to 5.0. The feed stream further contains 4 to 20 mol percent carbon dioxide, and the ratio of carbon dioxide to carbon (Continued)

monoxide in the feed stream is in a range from 0.5 to 4. The at least one synthesis step is carried out under isothermal conditions. A system for production of dimethyl ether (DME) from synthesis gas (SG) is likewise subject matter of the present invention.

19 Claims, 4 Drawing Sheets

(51) Int. Cl.
*C07C 27/06* (2006.01)
*C07C 43/04* (2006.01)

(56) References Cited

OTHER PUBLICATIONS

English machine translation of Notification of reasons of refusal for corresponding JP appln. 2016-549097 dated Nov. 26, 2018 (pp. 1-3).
Letter with additional English translation of Image text box #3 within JP2001070793.
Decision on Grant dated Nov. 28, 2018 issued in corresponding RU 2016134895104 (054502) application (5 pages).
English Abstract of RU 2375407 C2 published Dec. 10, 2009.
English Abstract of RU 2442767 C1 published Feb. 20, 2012.

\* cited by examiner

METHOD AND SYSTEM FOR OBTAINING DIMETHYL ETHER FROM SYNGAS

CROSS-REFERENCE TO RELATED APPLICATIONS

This application claims priority under 35 USC § 119 to International Patent Application No. PCT/EP2015/000007, filed on Jan. 5, 2015, which claims priority from European Patent Application EP 14 000 295.7, filed on Jan. 28, 2014.

BACKGROUND OF THE INVENTION

The invention relates to a process and a system for production of dimethyl ether from synthesis gas in which at least one feed stream formed from synthesis gas (SG) is subjected to at least one synthesis step, in which components present in the feed stream are at least in part converted to dimethyl ether (DME), wherein at least one crude product stream is obtained which contains at least dimethyl ether (DME) and unreacted components of the feed stream, characterized in that the feed stream contains hydrogen, carbon monoxide and carbon dioxide corresponding to a stoichiometric number of 2.1 to 5.0 and contains 4 to 20 mol percent carbon dioxide, in that the ratio of carbon dioxide to carbon monoxide in the feed stream is in a range from 0.5 to 4, and in that the at least one synthesis step is carried out under isothermal conditions.

Dimethyl ether (DME) is the structurally simplest ether. Dimethyl ether contains two methyl groups as organic radicals. Dimethyl ether is polar and is conventionally used in liquid form as a solvent. Dimethyl ether can in addition be used as coolant, and replace conventional fluorochlorohydrocarbons.

Recently, dimethyl ether is increasingly being used as a substitute for fuel gas (liquid gas) and conventional motor fuels such as diesel. Owing to its comparatively high cetane number of 55 to 60, conventional diesel engines, for example, need only be modified slightly for operation with dimethyl ether. Dimethyl ether burns comparatively cleanly and without soot formation. If dimethyl ether is prepared from biomass, it is considered to be what is termed biofuel, and can therefore be marketed with tax advantages.

Dimethyl ether can either be generated directly from methanol, or indirectly from natural gas or biogas. In the latter case, the natural gas or biogas is first reformed to give synthesis gas. Synthesis gas can also be produced by means of other processes, for example by pyrolysis of waste or biomass. The synthesis gas is classically converted to methanol, and subsequently further converted to dimethyl ether. The production of dimethyl ether from synthesis gas is thermodynamically and economically advantageous compared with production from methanol.

The present invention relates to the single-stage or direct production of dimethyl ether from synthesis gas. A single-stage or direct production is here taken to mean production without an intermediate separation off of methanol, as proceeds in a two-stage production. The reactions that proceed, however, can also deliver methanol as an intermediate in a single-stage production, which methanol, however, further reacts at least in part to form dimethyl ether in the reactor or reactors used. Corresponding processes have been known for a relatively long time and are also described in more detail hereinafter.

US 2013/0030063 A1 relates to a process for the direct synthesis of dimethyl ether from synthesis gas in an isothermally operated reactor. Unreacted synthesis gas present in the reactor off-stream can be recirculated to the reactor. For this purpose, the reactor off-stream is first cooled, in such a manner that the predominant fraction of the water and of the methanol and also about 40% of the dimethyl ether condense out. The remainder of the dimethyl ether and the predominant fraction of the carbon dioxide are lashed by means of an absorber using methanol as absorbent. Finally, a recycle stream depleted in a complex manner in carbon dioxide and a fresh feed are fed to the reactor, where a stoichiometric number of the gas mixture reacted in the reactor is maximally at a value of 2.05 and the ratio of carbon dioxide to carbon monoxide thereof is maximally 0.25.

In the preparation of dimethyl ether, the Topsøe process which is considered in EP 1 026 141 A1 and described in more detail hereinafter can also be used. The Topsøe process and other processes for preparation of dimethyl ether are also mentioned, for example, in the article "DME—the new wonder fuel?", Nitrogen & Methanol 260, 2002, pages 25 to 31.

There is still the requirement for a more flexible and more efficient process and systems for the production of dimethyl ether from synthesis gas.

SUMMARY OF THE INVENTION

Against this background, the present invention proposes a process and a system for production of dimethyl ether from synthesis gas in which at least one feed stream formed from synthesis gas (SG) is subjected to at least one synthesis step, in which components present in the feed stream are at least in part converted to dimethyl ether (DME), wherein at least one crude product stream is obtained which contains at least dimethyl ether (DME) and unreacted components of the feed stream, characterized in that the feed stream contains hydrogen, carbon monoxide and carbon dioxide corresponding to a stoichiometric number of 2.1 to 5.0 and contains 4 to 20 mol percent carbon dioxide, in that the ratio of carbon dioxide to carbon monoxide in the feed stream is in a range from 0.5 to 4, and in that the at least one step is carried out under isothermal conditions. Preferred embodiments are subject matter of the subclaims, and also of the description hereinafter.

Before the explanation of the features and advantages of the present invention, the fundamentals thereof and the expressions used will be explained.

If hereinafter production of dimethyl ether is briefly considered, this is taken to mean a process in which a feed containing the known components of synthesis gas, that is to say a gas mixture which contains, in suitable fractions, at least carbon monoxide, carbon dioxide and hydrogen, is reacted to form a product stream containing dimethyl ether. A corresponding product stream, owing to the incomplete reaction, and owing to the occurrence of side reactions in the synthesis of dimethyl ether, in particular depending on the characteristics of the catalysts used and the respective contents of the components of the synthesis gas, does not contain solely dimethyl ether, but rather other compounds. These are at least methanol, water, carbon dioxide, carbon monoxide and hydrogen, but also relatively small amounts of methane, ethane, organic acids and higher alcohols. These further compounds must at least in part be separated off in order firstly to permit subsequent separation steps and secondly to produce dimethyl ether in the purity required.

A fluid (the term fluid is also used in brief hereinafter for corresponding streams, fractions etc.) is derived from another fluid (which is here also termed starting fluid) or is formed from such a fluid when it has at least some of the components present in the starting fluid or obtained therefrom. A fluid which is derived or formed in this sense can be obtained or be formed from the starting fluid by separating off or branching off a fraction or one or more components, enrichment or depletion with respect to one or more components, chemical or physical conversion of one or more components, heating, cooling, pressurizing and the like. A stream can also, for example, simply be formed by the fact that it is taken off from a storage container.

Fluids, in the usage employed here, can be rich or poor in one or more components present, wherein rich can be a content of at least 50%, 60%, 70%, 80% or 90%, and poor can be a content of at most 50%, 40%, 30%, 20% or 10%, on a molar, weight or volume basis. In the usage employed here, they can be enriched or depleted in one or more components, wherein these expressions relate to a corresponding content in a starting fluid from which the fluid was formed. The fluid is enriched when it contains at least 1.1 times, 1.5 times, 2 times, 5 times, 10 times, 100 times or 1000 times the content, and is depleted when it contains at most 0.9 times, 0.5 times, 0.1 times, 0.01 times or 0.001 times the content of a corresponding component, based on the starting fluid. A fluid containing predominantly one or more components contains these one or more components at at least 50%, 60%, 70%, 80% or 90%, or is rich therein in the meaning of the above definition.

Hereinafter, for characterizing pressures and temperatures, the expressions pressure level and temperature level are used, whereby it must be stated that pressures and temperatures need not be used in the form of exact pressure or temperature values in order to realize an inventive concept. However, such pressures and temperatures are typically in certain ranges which are, for example, ±1%, 5%, 10%, 20% or even 50% about a mean. Differing pressure levels and temperature levels can in this case be in disjoint ranges or in ranges which overlap one another. In particular, pressure levels, for example, include unavoidable or expected pressure drops, for example owing to cooling effects. The same applies to temperature levels. The pressure levels stated here in bar are absolute pressures.

Dimethyl ether can, as already stated at the outset, be produced by a two-stage synthesis from synthesis gas via methanol as intermediate. Corresponding processes are described, for example, from page 171 in the DME Handbook of the Japan DME Forum, ISBN 978-4-9903839-0-9, 2007. The two-stage production of dimethyl ether from synthesis gas is, as mentioned, characterized in that first methanol is produced from synthesis gas, then the unreacted synthesis gas is separated off from the condensates (methanol and water) and the methanol is then dehydrated in a further reactor with production of dimethyl ether and water.

To produce dimethyl ether, usually upright tubular reactors are used which are charged in each case from the bottom with pressurized heated synthesis gas. A resultant product stream is taken off at the top, cooled, and fed to a separation.

The production of dimethyl ether in a two-stage process is expensive (and energetically costly), since for this purpose a complete system is required for generating methanol as intermediate in addition to equipment for the production of dimethyl ether from the methanol.

In the patent literature, as early as 1973 (DE 23 62 944 A1, U.S. Pat. No. 4,098,809 A), the direct or single-stage production of dimethyl ether from synthesis gas is described. This is distinguished by a shared reaction stage where methanol and dimethyl ether are jointly produced from hydrogen, carbon monoxide and carbon dioxide. Further processes based thereon have been described in the literature.

In a known combined process, what is termed the Topsøe process, as is described in the DME Handbook from page 185, in particular on page 187, but also, for example, in cited EP 1 026 141 A1, a dual catalyst where both methanol and dimethyl ether may be formed is used. At least two reactors without intermediate separation are used, wherein a first reactor is cooled isothermally and a second reactor is operated adiabatically. A synthesis gas having a stoichiometric number (see below) of approximately 2 is used. Parallel production of dimethyl ether and methanol proceeds, wherein the methanol can be converted to dimethyl ether in a further reactor after separation of the components. In the Topsøe process, more and more reactors are provided (isothermally and adiabatically operated). In addition, the methanol produced in relatively large amounts needs to be converted in a further reactor to dimethyl ether, if simultaneous production of methanol is not desired.

In the Topsøe process, in the reactors in which only one (copper-based) catalyst is used for methanol synthesis, carbon dioxide can be formed only to a slight extent. Although a corresponding catalyst in this case in principle catalyses not only the reaction $2\ H_2+CO \rightarrow CH_3OH$ but also the reaction $H_2O+CO \rightarrow H_2+CO_2$ (termed the watergas shift), the watergas shift proceeds scarcely at all or at any rate to a small extent in the Topsøe process, since water is scarcely present in the reactor feed. Usually, the synthesis gas and also the recycle streams are cooled to 30 to 40° C. before and between the compression stages in the Topsøe process, and the condensate is removed. Catalysts used in the Topsøe process for the synthesis of dimethyl ether, on the other hand, catalyse the reaction $2\ CH_3OH \rightarrow CH_3OCH_3+H_2O$. If, therefore, in a corresponding adiabatic reaction stage, a catalyst is used in parallel for the methanol synthesis, the watergas shift, on account of the water formed, can proceed to a small extent, and small amounts of carbon dioxide form. Principally, however, methanol is further formed. If, in a corresponding adiabatic reaction stage, only one catalyst is used for the synthesis of dimethyl ether, no carbon dioxide is formed, since the catalyst is not competent to form the watergas shift.

As a result of the reactor configuration of the Topsøe process, substantially less carbon dioxide is formed than in the case of a single isothermally cooled reaction step using a mixed catalyst, as underlies the present invention. Owing to the solubility of carbon dioxide, this is additionally typically removed in the methanol, as already described hereinbefore with reference to US 2013/0030063 A1. In total, therefore, in the Topsøe process, little or no carbon dioxide is formed, in such a manner that neither the high carbon dioxide contents used according to the invention nor the high ratios of carbon dioxide to carbon monoxide are present in a corresponding feed stream (see hereinafter), which are an important feature and control instrument in the context of the present invention.

The direct synthesis of dimethyl ether can also proceed, for example, in the slurry mode of operation and at relatively low stoichiometric numbers (see hereinafter). However, as a result, carbon dioxide is always formed as a byproduct which must be separated off from the respective unreacted compounds, in order to be able to feed the latter back to the reaction as recycle. The said reactions here proceed with a satisfactory yield only at a low carbon dioxide content.

The invention proposes a process for production of dimethyl ether from synthesis gas, in which at least one feed stream formed from synthesis gas is subjected to at least one synthesis step, in which components present in the feed stream are at least in part converted to dimethyl ether. In this case, at least one crude product stream is obtained which contains at least dimethyl ether and unreacted components of the feed stream.

The invention is therefore used in a single-stage production of dimethyl ether. As mentioned, in the case of a two-stage production of dimethyl ether via the intermediate methanol, the latter is separated off and reacted, isolated, further to dimethyl ether. Therefore, as in the context of the present invention, no crude product stream is obtained which contains at least dimethyl ether and unreacted components of the feed stream.

If here, it is mentioned that a feed stream is formed from synthesis gas, this comprises, in particular, also the admixture of further components to a synthesis gas stream, as already stated hereinbefore. The feed stream itself is that which is subjected, after an admixture, to the at least one synthesis step.

According to the invention, it is provided that the feed stream contains at least hydrogen, carbon monoxide and carbon dioxide corresponding to a stoichiometric number of 2.1 to 5.0, wherein the carbon dioxide content is 4 to 20 mol percent, in that the ratio of carbon dioxide to carbon monoxide in the feed stream is in a range from 0.5 to 4, and in that the at least one synthesis step is carried out under isothermal conditions. In particular, the synthesis can proceed in a single isothermally operated reactor, but it is also possible to use a plurality of isothermally operated reactors, which can operate at differing temperature levels.

Particularly advantageously, in the context of the present invention, isothermally operated cooled fixed-bed reactors are used. Compared with other reactor types, for example fluidized-bed reactors, as are used in US 2013/0030063 A1, in order to obtain approximately isothermal conditions, said fixed-bed reactors, in the context of the present invention, offer particular advantages. In contrast to a fluidized-bed reactor, in a fixed-bed reactor, the heat of reaction can generally be removed somewhat more poorly. As a result, a person skilled in the art would at first not consider the use of a corresponding reactor for employment in an isothermal reaction. However, as a result of the present specific reaction conditions according to the invention (higher carbon dioxide/carbon monoxide ratio and higher stoichiometric number), firstly the heat of reaction is lower, and secondly, more dilution gas is present in the reactor. In this manner, the temperature and, in particular what are termed "hot spots", can be controlled in the reactor.

Generally, the feed stream is formed from synthesis gas, the stoichiometric number of which is above 2.0, for example 2.05. The feed stream, however, can also be formed from synthesis gas, the stoichiometric number of which is below 2.0, for example 1.7. This can proceed, for example, in the admixture of a synthesis gas stream having a high stoichiometric number, or when a carbon dioxide-rich stream 8 shown in FIGS. 2 to 4 is ejected. The feed stream ultimately formed is distinguished, however, according to the invention by said stoichiometric number of 2.1 to 5.0. All statements with respect to the stoichiometric numbers used according to the invention relate to the feed stream, which is actually subjected to the at least one synthesis step. Corresponding carbon dioxide contents are established when a carbon dioxide-containing recycle stream is used for forming the feed stream, even if the synthesis gas stream used is carbon dioxide poor.

The stoichiometric number in this case is in particular 2.1 to 4.8, for example 2.2 to 2.4, 2.4 to 2.6, 2.6 to 2.8, 2.8 to 3.0, 3.0 to 3.2, 3.2 to 3.4, 3.4 to 3.6, 3.6 to 3.8, 3.8 to 4.0, 4.0 to 4.2, 4.2 to 4.4, 4.4 to 4.6, or 4.6 to 4.8.

For characterization of the synthesis gas used for the production of dimethyl ether, or else of feed streams formed from synthesis gas and recycle streams, frequently the said stoichiometric number SN is used. For this, $SN=(xH_2-xCO_2)/(xCO+xCO_2)$ applies, wherein x is the molar content of the components hydrogen ($H_2$), carbon monoxide (CO) and carbon dioxide ($CO_2$). The reactions observed in the conventional production of dimethyl ether directly from synthesis gas may be stated as follows:

$$3\ H_2 + 3\ CO \rightarrow CH_3OCH_3 + CO_2 \tag{1}$$

$$4\ H_2 + 2\ CO \rightarrow 2\ CH_3OH \rightarrow CH_3OCH_3H_2O \tag{2}$$

The stoichiometric number considered as ideal in conventional processes results therefrom according to reaction equation (1) as $$SN=(3\ mol\ H_2-0\ mol\ CO_2)/(0\ mol\ CO+3\ mol\ CO_2)$$
$$=1.0$$

and according to reaction equation (2) as $$SN=(4\ mol\ H_2-0\ mol\ CO_2)/(2\ mol\ CO+0\ mol\ CO_2)$$
$$=2.0.$$

In the reaction according to reaction equation (1) and where SN=1.0, virtually a complete conversion of the components used can be achieved step by step. However, the carbon dioxide formed must for this purpose be conducted again through a reformer and be converted there to carbon monoxide. This is decidedly costly in energy. Carbon dioxide is therefore unwanted in conventional processes which operate at correspondingly low stoichiometric numbers, because it can inhibit the participating reactions. Therefore it must be separated off in a costly manner.

In contrast, in a reaction according to reaction equation (2) and SN=2.0, there is per passage a lower conversion rate and water forms, in which hydrogen and oxygen are bound which can be converted according to reaction equation (1) completely to the desired product.

As mentioned, in the production of dimethyl ether from synthesis gas, even when the respective "ideal" stoichiometric number is maintained, the components present are never completely converted, and in addition the said reactions proceed, even if in differing fractions, parallel to one another. Therefore, in the crude product obtained, that is to say at the outlet of the reactor or reactors used, carbon dioxide is also always found which forms, in particular, at low stoichiometric numbers.

The present invention is then based at least in part on the knowledge that this carbon dioxide, at higher stoichiometric numbers, together with the unreacted components, can be recirculated to the reactor or reactors used, because it can likewise be converted. It need therefore not be separated off in a costly manner, if a corresponding recycle stream is to be used. The same also applies to a synthesis gas used to form the feed stream. This also always has a certain amount of carbon dioxide which, in the context of the present invention, need not be separated off, or at least need only be separated off to a smaller extent.

In the context of the present invention, it has turned out, that for production of dimethyl ether, the reaction hereinafter, for example, can also be used:

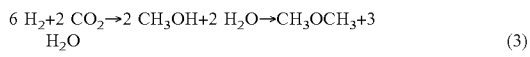

$$6\ H_2 + 2\ CO_2 \rightarrow 2\ CH_3OH + 2\ H_2O \rightarrow CH_3OCH_3 + 3\ H_2O \tag{3}$$

The stoichiometric ratios present in the reaction according to equation (3) correspond to a stoichiometric number of SN=(6 mol H$_2$−2 mol CO$_2$)/(0 mol CO+2 mol CO$_2$)
=2.0 and therefore to that according to reaction equation (2). However, in the case of still higher stoichiometric numbers, as are used in the context of the present invention, a markedly higher conversion rate of carbon dioxide and carbon monoxide to dimethyl ether may be observed.

The high stoichiometric numbers of the present invention are achieved, for example, by a recycle of the unreacted components of the synthesis gas in combination with a make-up, that is to say, e.g. fresh synthesis gas, having a stoichiometric number slightly above two, for example at SN=2.05. As a result of the recycle, excess hydrogen concentrates step by step. The stoichiometric number increases thereby, even if carbon dioxide is recycled. The stoichiometric number of the feed stream finally present at the reactor intake, that is to say of the stream which is actually converted in the reactor and is composed of fresh synthesis gas and optionally a recycle stream, is therefore at least 2.1.

The advantages of the present invention are given, in particular, by a combination of the abovementioned aspects: Because here carbon dioxide need not be converted in a reformer to form carbon monoxide, an advantage in the overall efficiency of the process results, even if, owing to the higher stoichiometric numbers used, lower conversion rates per passage may be achieved. The latter are also compensated for by the still higher stoichiometric numbers. In other words, the overall process is markedly more efficient, because carbon dioxide can be utilized and need not be recycled.

As a result of the process procedure according to the invention, in which, preferably only one isothermally cooled reactor is used, further advantages over known processes are given such as the Topsøe process mentioned, in which two differently (isothermally and adiabatically) operated reactors are always used.

The isothermal process procedure is therefore also advantageous because in the cooling of the corresponding reactor, steam can be produced which is available for other purposes, for example for a feed preheating.

The contents of carbon dioxide and carbon monoxide in the context of the process according to the invention can also be stated via the ratio of these compounds to one another. The carbon dioxide/carbon monoxide ratio in this case is above 0.5, in particular 0.5 to 4, for example 0.5 to 3, or 0.5 to 2, in particular 0.5 to 1.0, 1.0 to 1.5, or 1.5 to 2.0.

In the context of the present invention, the ratio of carbon dioxide to carbon monoxide is of particular importance, inter alia in order to influence the equilibrium of the above-explained watergas shift, but also to control the reaction rate.

As a result of the general use of high carbon dioxide contents in a reactor feed, in the context of the present invention, a substantially higher energy and carbon efficiency is achieved than in the prior art. In the context of the present invention, this is owing to the fact that, as described above, carbon dioxide is converted to dimethyl ether in the reactor used. The advantages of the invention are in this case particularly pronounced in the case of light feeds such as methane or natural gas for synthesis gas production. In the cited prior art, in contrast, carbon or biomass are used as feeds.

In the context of the invention, therefore, a resultant crude product stream can be recirculated completely to the reaction without separating off carbon dioxide (but after separating off the desired products, for example dimethyl ether). The process according to the invention therefore proves to be simpler in realization.

According to the invention, it is further provided, as mentioned, to use only isothermally operated reactors. As a result, only a single reactor needs to be provided; the use of reactors operated differently (isothermally and adiabatically), in contrast, is no longer required.

The process according to the invention can also comprise a synthesis via methanol as intermediate, wherein the latter, however, is not separated off. Therefore, costly separation appliances can be dispensed with. Therefore, in the at least one synthesis step (for example in only one reactor), hydrogen and carbon monoxide are first converted to methanol and the methanol thereafter is further converted to dimethyl ether in the presence of the components present in the feed stream. In the context of the process according to the invention, methanol separated off from a crude product stream can also be recirculated to the synthesis step. As a result, a reactor which is conventionally used for dehydration of methanol to form dimethyl ether, can be spared.

As mentioned, advantageously, from the crude product stream, the unreacted components of the feed stream are at least in part separated off and recirculated. They can in this case be used together with the synthesis gas to form the feed stream. In this case, for example a shared compression of a synthesis gas stream and of a corresponding recycle stream can proceed, as a result of which separate compressor stages can be dispensed with. Such a shared compression is also present when the recycle stream is fed in between two compressor stages of a compressor, through which the synthesis gas stream flows completely.

In particular, from the crude product stream, the unreacted components of the feed stream can be added in a recycle stream predominantly containing hydrogen, carbon monoxide and carbon dioxide at least in part to a synthesis gas stream. Separating off carbon dioxide is, as mentioned, not necessary, or not completely necessary, in such a manner that a process according to the invention is favourable economically and energetically.

It can also prove advantageous in addition to produce a methanol stream from the crude product stream and to add said methanol stream at least in part together with the recycle stream to the synthesis gas stream. As a result, methanol present in the methanol stream can be converted further to dimethyl ether in parallel to the direct production of dimethyl ether from the synthesis gas.

In the context of the process according to the invention, the at least one synthesis step is advantageously carried out at a temperature level of 190 to 310° C. and/or at a pressure level of 20 to 100 bar. Under corresponding conditions, in particular a pressure level above 50 bar, the above described reaction steps proceed particularly efficiently. In contrast thereto, according to the prior art previously cited above, markedly lower pressure levels are used.

In the context of the process according to the invention, in the at least one synthesis step, advantageously at least one catalyst is used which is able to form dimethyl ether from the said starting compounds via methanol as intermediate, for example a copper-zinc catalyst. This also operates effectively under the stated conditions.

The invention is suitable in particular for processes in which, from the crude product stream, in addition, water, dimethyl ether, carbon dioxide and/or methanol are separated off. The resultant components can, according to requirements, be used in a process employed as also described hereinafter.

A system for production of dimethyl ether from synthesis gas is likewise subject matter of the present invention. The system has at least one dimethyl ether reactor which is equipped to subject at least one feed stream formed from synthesis gas to at least one synthesis step in which components that are present in the feed stream are at least in part converted to dimethyl ether. This therefore concerns at least one dimethyl ether reactor used for the single-stage production of dimethyl ether. If a plurality of dimethyl ether reactors are present, these can be arranged in series or in parallel and be charged with one or more feed streams.

In the single-stage production of dimethyl ether, as already explained, at least one crude product stream is obtained which contains at least dimethyl ether, methanol and water, and the unreacted components of the feed stream. According to the invention. such a system is distinguished by means which are equipped to form the feed stream in such a manner that the latter has at least hydrogen, carbon monoxide and carbon dioxide according to a stoichiometric number of 2.1 to 5.0, in that the ratio of carbon dioxide to carbon monoxide in the feed stream is in a range from 0.5 to 4, and contains at least 4 to 20 mol percent carbon dioxide. In addition, according to the invention, at least one cooling appliance is provided which is equipped to operate the at least one dimethyl ether reactor during the at least one synthesis step isothermally. As mentioned, the reactions for forming dimethyl ether proceed exothermally, in such a manner that, for an exclusively isothermal operation of the reactor or reactors used, a corresponding heat removal must be ensured.

Such a system is equipped, in particular, for carrying out a process as has been extensively explained hereinbefore. The system according to the invention profits from the explained advantages, to which reference is therefore explicitly made.

The invention will be described in more detail with reference to the drawings which show embodiments of the invention.

DETAILED DESCRIPTION OF THE INVENTION

Figure 1:
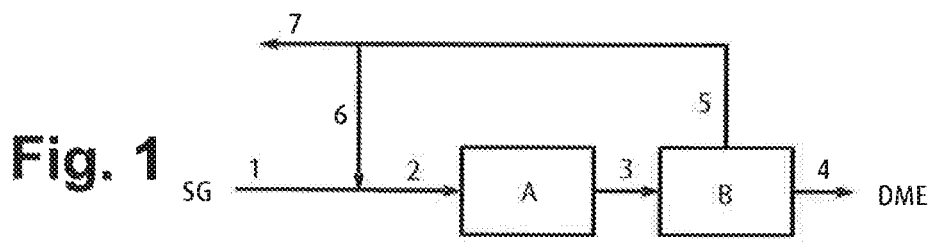
FIG. 1 shows a process for production of dimethyl ether from synthesis gas according to one embodiment of the invention in a schematic depiction

In the figures, elements corresponding with one another are given with identical reference signs, and for the sake of clarity are not described repeatedly.

FIGS. 1 to 4 show embodiments of a process according to the invention for production of dimethyl ether DME from synthesis gas SG. A synthesis step which can proceed in one or more isothermally operated reactors is designated A and a separation step is designated B. All of the embodiments shown have in common the fact that a synthesis gas stream 1, after combination with at least one further stream, is subjected as feed stream 2 to the synthesis step A.

The synthesis gas stream 1 can contain synthesis gas SG from one or more suitable upstream process steps (for example from steam reforming, autothermal reforming, dry reforming, or partial oxidation). The synthesis gas stream 1 contains hydrogen, carbon monoxide and carbon dioxide, and typically also minor components such as methane and nitrogen.

To form the feed stream 2, the synthesis gas stream 1 (make-up stream), in contrast to conventional processes for single-stage production of dimethyl ether from synthesis gas, is not freed from carbon dioxide or is only partially freed from carbon dioxide. To form the feed stream 2, the synthesis gas stream 1 is additionally mixed with at least one recycle stream 6 which is formed from the components produced in the separation step B. The recycle stream 6 can either be compressed in a recycle compressor in such a manner that the synthesis gas stream 1 and the recycle stream 6 are present at the same pressure level, or it is compressed together with the synthesis gas stream 1. In this case, the recycle stream 6 contains at least some of the components of the synthesis gas stream 1 or of the feed stream 2, unreacted in the synthesis step A. The feed stream 2 is distinguished in the illustrated embodiment of the invention from the prior art by a comparatively high stoichiometric number and a comparatively high carbon dioxide content, as stated hereinbefore.

In the synthesis step A, a dimethyl ether-containing crude product stream 3 is produced from the feed stream 2. The crude product stream 3, in addition to dimethyl ether, can also contain unreacted synthesis gas, methanol, water, and possibly (at least in synthesis step (A)) inert gases. It is subjected to the separation step B, in which at least one product stream 4 predominantly containing dimethyl ether is produced. The product stream 4, in addition to dimethyl ether, can also contain relatively large amounts of methanol and water, and also impurities such as carbon dioxide and alkanes. The purity generated is based on economic considerations.

In the embodiment of the invention shown in FIG. 1, in addition to the product stream 4, an off-stream 5 of unreacted synthesis gas SG or the unreacted components of the synthesis gas stream 1 or of the feed stream 2 is obtained. The off-stream 5 predominantly contains hydrogen, carbon monoxide, carbon dioxide, methane, and further light inert gases. The off-stream 5 is divided, obtaining the recycle stream 6 and a residual stream 7, wherein the residual stream 7 is usually formed of only 1 to 10% of the off-stream 5. The residual stream 7 can be used as fuel gas, e.g. in the burner of a reformer, for producing the synthesis gas SG, as feed in such a reformer, for generation of a hydrogen-rich stream, e.g. by pressure-swing absorption, as product export and/or in other system parts, for example for natural gas desulphurization upstream of a reformer.

Figure 2:
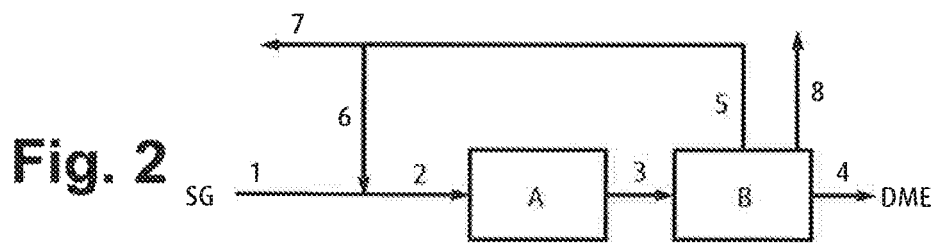
FIG. 2 shows a process for production of dimethyl ether from synthesis gas according to one embodiment of the invention in a schematic depiction

In FIG. 2, a further embodiment of the invention is shown in which a carbon dioxide-rich stream 8 arises in the separation step B. The carbon dioxide present in this carbon dioxide-rich stream 8, for example at at least 80%, is found according to FIG. 1 in the off-stream 5. The carbon dioxide can therefore, depending on the configuration of the separation unit B, either be obtained together with further components (FIG. 1) or as a separate stream 8 (FIGS. 2 to 4) and in this case be present in gaseous or liquid state. The stream 8 can be mixed, for example, with the off-stream 5 (optionally after pressure elevation), recycled as feed for generating the synthesis gas SG, mixed with the synthesis gas stream 1 before or during a compression, and/or employed, e.g. in the burner of a reformer, to produce the synthesis gas SG. The provision of a separate stream 8 therefore increases the flexibility.

Figure 3:
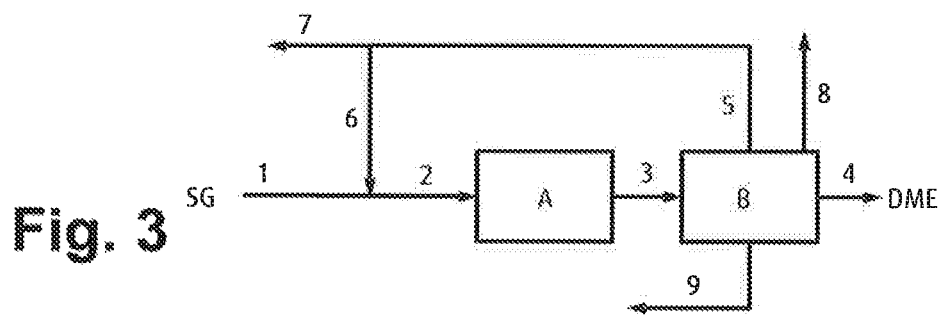
FIG. 3 shows a process for production of dimethyl ether from synthesis gas according to one embodiment of the invention in a schematic depiction

In FIG. 3, a further embodiment of the invention is shown, in which a methanol- and/or water-rich stream 9 arises in the separation step B. In this embodiment of the invention, the product stream 4 can be particularly rich in dimethyl ether and poor in methanol and/or water. The methanol- and/or water-rich stream 9 can be recycled for the production of the synthesis gas SG.

Figure 4:
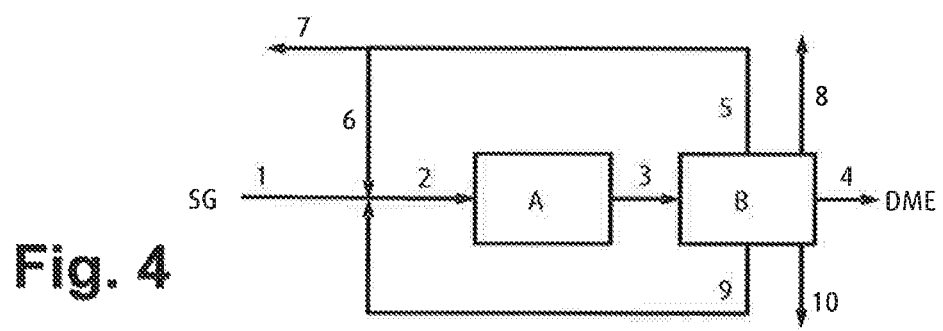
FIG. 4 shows a process for production of dimethyl ether from synthesis gas according to one embodiment of the invention in a schematic depiction

In FIG. 4, a further embodiment of the invention is shown, in which a methanol-rich stream 9 and a water-rich stream 10 arise separately in the separation step B. The methanol-rich stream 9 can be exported, or recycled for production of the synthesis gas SG. The methanol-rich stream 9 can also be recirculated to the synthesis step A and employed for formation of dimethyl ether. No further reactor for the dehydration of the methanol is required. The water-rich stream 10 can be subjected to a wastewater treatment.

What we claim is:

1. A process for production of dimethyl ether from synthesis gas, said process comprising:
    subjecting at least one feed stream formed from synthesis gas to at least one synthesis step wherein components present in the at least one feed stream are at least in part converted to dimethyl ether, and
    obtaining at least one crude product stream which contains at least dimethyl ether and unreacted components of the at least one feed stream,
    wherein said at least one feed stream contains hydrogen, carbon monoxide and carbon dioxide corresponding to a stoichiometric number of 2.1 to 5.0 and contains 4 to 20 mol percent carbon dioxide, and the molar ratio of carbon dioxide to carbon monoxide in the at least one feed stream is in a range from 0.5 to 4,
    wherein unreacted components of the at least one feed stream are, at least in part, separated from the crude product stream, and said unreacted components are used together with the synthesis gas to form the at least one feed stream, and
    wherein the at least one synthesis step is carried out under isothermal conditions.

2. The process according to claim 1, wherein in said at least one synthesis step hydrogen, carbon monoxide and/or carbon dioxide are converted to methanol, and the methanol is further converted to dimethyl ether in the presence of other components present in the at least one feed stream.

3. The process according to claim 1, wherein the unreacted components of the at least one feed stream are added at least in part to a synthesis gas stream as a recycle stream which predominantly contains hydrogen, carbon monoxide and carbon dioxide.

4. The process according to claim 3, wherein a methanol stream is produced from the crude product stream, and the methanol stream is added at least in part together with the recycle stream to the synthesis gas stream.

5. The process according to claim 1, wherein the at least one synthesis step is carried out at a temperature level of 190 to 310° C. and at a pressure level of 20 to 100 bar.

6. The process according to claim 1, wherein, in the at least one synthesis step, at least one catalyst is used to form dimethyl ether from hydrogen and carbon monoxide, and from hydrogen and carbon dioxide via methanol as intermediate.

7. The process according to claim 1, further comprising separating off water, dimethyl ether, carbon dioxide and/or methanol from the crude product stream.

8. The process according to claim 1, wherein the at least one synthesis step is carried out at a temperature level of 190 to 310° C.

9. The process according to claim 1, wherein the at least one synthesis step is carried out at a pressure level of 20 to 100 bar.

10. The process according to claim 1, wherein the at least one synthesis step is carried out in an isothermally operated cooled fixed-bed reactor.

11. The process according to claim 1, wherein the molar ratio of carbon dioxide to carbon monoxide in the at least one feed stream is in a range from 0.5 to 2.0.

12. The process according to claim 1, wherein the molar ratio of carbon dioxide to carbon monoxide in the at least one feed stream is in a range from 0.5 to 1.0.

13. The process according to claim 1, wherein the molar ratio of carbon dioxide to carbon monoxide in the at least one feed stream is in a range from 1.0 to 1.5.

14. The process according to claim 1, further comprising subjecting said crude product stream to a separation step wherein a product stream predominantly containing dimethyl ether and a recycle stream of unreacted components of the at least one feed stream are obtained.

15. The process according to claim 1, further comprising subjecting said crude product stream to a separation step wherein a product stream predominantly containing dimethyl ether, a carbon dioxide-rich stream, and a recycle stream of unreacted components of the at least one feed stream is obtained.

16. The process according to claim 1, wherein said at least one feed stream contains hydrogen, carbon monoxide and carbon dioxide corresponding to a stoichiometric number of 3.6 to 4.8.

17. The process according to claim 1, wherein said at least one feed stream contains hydrogen, carbon monoxide and carbon dioxide corresponding to a stoichiometric number of 4.0 to 4.8.

18. The process according to claim 1, wherein the at least one synthesis step is carried out at a pressure level of greater than 50 bar to 100 bar.

19. A process for production of dimethyl ether from synthesis gas, said process comprising:
    subjecting at least one feed stream formed from synthesis gas to at least one synthesis step wherein components present in the at least one feed stream are at least in part converted to dimethyl ether, and
    obtaining at least one crude product stream which contains at least dimethyl ether and unreacted components of the at least one feed stream,
    wherein said at least one feed stream contains hydrogen, carbon monoxide and carbon dioxide corresponding to a stoichiometric number of 2.1 to 5.0 and contains 4 to 20 mol percent carbon dioxide, and the molar ratio of carbon dioxide to carbon monoxide in the at least one feed stream is in a range from 0.5 to 4, and
    wherein the at least one synthesis step is carried out under isothermal conditions in an isothermally operated cooled fixed-bed reactor.

* * * * *